United States Patent [19]

Sauska et al.

[11] Patent Number: 5,230,792
[45] Date of Patent: Jul. 27, 1993

[54] ULTRAVIOLET WATER PURIFICATION SYSTEM WITH VARIABLE INTENSITY CONTROL

[75] Inventors: Christian Sauska, 277 Argyle Rd., Orange, Conn. 06477; George Csoknyai, 25 Wellington Dr., Orange. Conn. 06477; David Packlocok, Sleepy Hollow, Ill.

[73] Assignees: Christian Sauska; George Csokneyai, both of Orange, Conn.

[21] Appl. No.: 469,203

[22] Filed: Jan. 24, 1990

[51] Int. Cl.⁵ .............................................. C02F 1/32
[52] U.S. Cl. ...................................... 210/97; 210/143; 210/243; 210/254; 210/748; 250/436; 250/437; 422/24
[58] Field of Search ................. 210/97, 143, 243, 259, 210/85, 103, 748; 422/24; 250/432 R, 436, 437

[56] References Cited

U.S. PATENT DOCUMENTS 4,400,270 6/1982 Hillman ............................ 210/103
4,769,131 9/1988 Noll et al. .............................. 210/85

Primary Examiner—Robert A. Dawson
Assistant Examiner—David Reifsnyder
Attorney, Agent, or Firm—Paul A. Fattibene; Arthur T. Fattibene

[57] ABSTRACT

An ultraviolet purification system in which ultraviolet radiation is generated by an ultraviolet lamp wherein the amount of ultraviolet radiation is varied in accordance with fluid flow. The intensity of the ultraviolet lamp is controlled by a circuit which is responsive to fluid flow for selectivity energizing the lamp to provide variable UV intensity output depending upon fluid flow. The circuit arrangement is such that the ultraviolet lamp is always started with a high current ballast. The selection of ultraviolet lamp intensity outputs according to fluid flow maximizes the useful life of the ultraviolet lamp and renders the system more efficient by reducing the amount of heat transmitted to the fluid being acted upon during periods of low flow or non-use.

8 Claims, 3 Drawing Sheets

ULTRAVIOLET WATER PURIFICATION SYSTEM WITH VARIABLE INTENSITY CONTROL

FIELD OF THE INVENTION

This invention relates generally to ultraviolet water purification systems and more particularly to an ultraviolet purification system having a variable intensity control arrangement to vary the amount of ultraviolet energy generated in response to fluid flow.

BACKGROUND OF THE INVENTION

Many systems have been developed to assist in the purification of water and other fluids. Many of these systems use active carbon filters or other filters of a mechanical nature to remove chemicals and other particular matter, including micro-organisms. Such filters, while capable of removing certain particular matter and chemicals, are not completely satisfactory for the purification of fluids and water containing bacteria type of contaminents.

It is well known that the exposure of water of fluids to ultraviolet radiation kills many micro-organisms and bacteria. One such ultraviolet purification system is disclosed in U.S. Pat. No. 4,769,131 entitled "Ultraviolet Radiation Purification System," and issued on Sep. 6, 1988. This patent discloses a water purification system using an ultraviolet lamp, and it is directed to two independent fluid conduits that are coiled about an ultraviolet lamp. The conduits are transparent permitting the ultraviolet energy to radiate the fluid flowing within the two conduits. Accordingly, any micro-organisms or bacteria present in the fluid so treated will be killed. In order to kill the micro-organisms contaminating water, a specific quantity or level of ultra-violet radiation must be maintained in order to effectively rid the contaminating micro-organisms from fluid or water being treated. The lamp, therefore, must provide the optimum amount of ultraviolet energy to kill the micro-organisms during the maximum rated fluid flow.

Heretofore, in ultraviolet water purification systems, in order to maintain the system in its optimum purification mode of operation, the energy source, i.e. the ultraviolet lamp was operated at its optimum operating mode regardless of the amount of fluid flow. Thus, at low flow or not flow rate, the ultraviolet lamp was maintained in its operating mode. The ultraviolet energy source or lamp was so maintained because the cycling of the lamp between "on" and "off" materially affected or shortened the useful life of the lamp.

In systems where the fluid flow was subjected to frequent intermittent flow operation, e.g. drinking water and/or other types of demand use situations, it was noted that the heat generated by the energized ultraviolet lamp source would be transmitted to the fluid or liquid being treated. In a low flow or no flow situation, the standing or slow moving water in the vicinity of the U.V. source or lamp would become highly heated, a very undesirable situation in the case of drinking water. The problem is even more aggravated during long periods of non flow of such water or fluid.

In applications involving frequent uses for short durations, the cycling on and off of the ultraviolet lamp has proven to shorten the lamp's life. Therefore, it is advantageous to eliminate as much as possible, the on and off cycling of the UV lamp.

In other systems, e.g. as disclosed in U.S. Pat. No. 4,767,932, successive banks of ultraviolet lamps were disposed in the path of fluid flow wherein the amount of ultraviolet radiation generated was determined by the number of lamp banks that were energized in accordance to fluid flow. Systems of this type have been utilized to treat waste fluids. In such systems, it was still necessary to subject the lamp to an on-off cycle, even though the lamps were actuated in banks.

OBJECTS

It is an object of the present invention to provide an efficient ultraviolet lamp purification system in which the amount of radiation generated by the UV source is varied.

It is another object of the present invention to prevent overheating of the fluid being purified by ultraviolet radiation.

It is yet another object of the present invention to provide an ultraviolet purification system in which the amount of ultraviolet radiation is varied without the "on"-"off" cycling of the ultraviolet radiation source.

It is an advantage of the present invention that the lamp intensity is controlled without cycling between "on" and "off" by the flow of fluid to be purified.

SUMMARY OF THE INVENTION

The foregoing objects, features and other advantages are obtained by an ultraviolet water purification system in which the energy source, i.e. the ultraviolet lamp, once activated, is at all times maintained in an energized state wherein the intensity or amount of ultraviolet radiation, emitted by the lamp and transmitted to the medium or fluid being acted upon, is varied in accordance to the amount and/or flow of the medium being acted upon. The arrangement is such that sufficient UV radiation is generated to effectively kill the micro-organism or bacteria in the medium to be treated during an operating or demand mode of the system, and wherein the lamp is maintained in a low UV generating state when the system is not in a demand mode or operating at a reduced level. This is attained by a control circuit that includes a starting ballast connected to a pre-heat circuit which is operatively connected to a circuit that insures activation of the starting ballast to initiate the energization of the UV lamp source, and which is then rendered responsive to fluid flow to vary the amount of UV radiated by the UV lamp in accordance to said fluid flow so that the lamp is maintained in an energized state of variable UV output as long as the control circuit is maintained activated.

FEATURES

A feature of this invention is to provide a UV purification system with a control circuit that will vary the amount of UV energy generated by the UV lamp source in accordance with fluid flow without cycling the lamp "on" and "off".

Another feature is to provide a control circuit for a UV lamp in a water purification system wherein the induction to the UV lamp circuit is increased to as to reduce the amount of UV radiation emitted in accordance with fluid flow.

Another feature is to provide a UV water purification system which will reduce or retard the amount of heat generated during a low mode or non-operating mode.

Another feature resides in a UV water purification system in which the control circuit for varying the amount of UV generation without cycling the lamp source "on" or "off" is relatively simple, positive and effective.

Other features and advantages will become more readily apparent when considered in view of the drawings and following detailed description.

IN THE DRAWINGS

DETAIL DESCRIPTION

Figure 1:
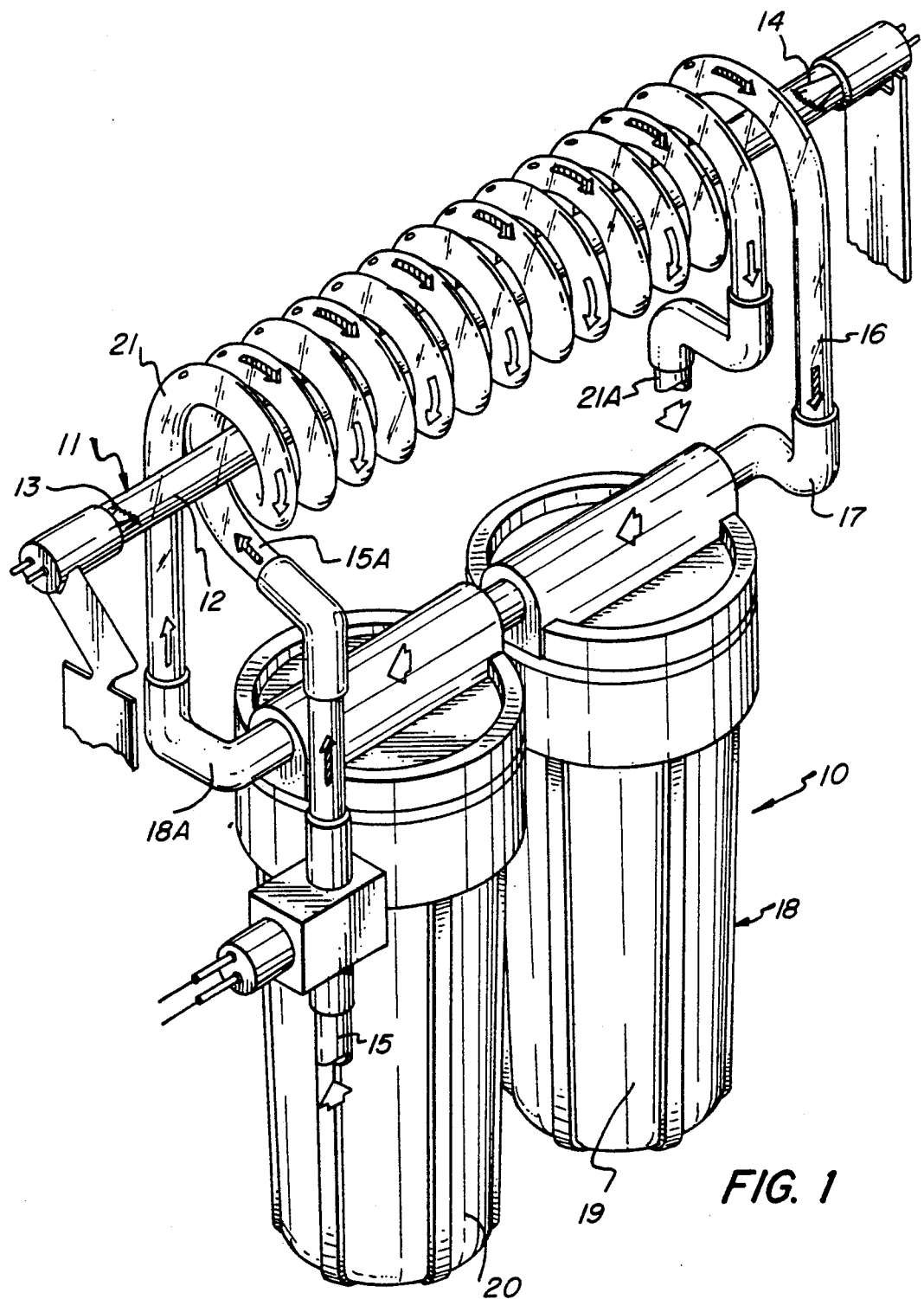
FIG. 1 is a perspective view of a water purification system embodying the invention.

Referring to the drawings, there is shown in FIG. 1 a water purification system 10 embodying the present invention. As shown, the water purification system comprises a source of UV radiation, e.g. an elongated ultraviolet lamp 11. The lamp 11 consists of an elongated tube 12 having electrodes 13 and 14 disposed in the opposed ends thereof. Water or liquid to be purified by UV radiation is directed from a suitable source or reservoir (not shown) to an inlet conduit 15. The conduit is preferably made of a clear or transparent material which is pervious to UV radiation. In the form of the invention disclosed in FIG. 1, the inlet conduit 15 is connected to a coil 15A of a UV pervious material, which is disposed about the UV lamp 11 in UV transmitting relationship. The outlet end 16 of the coil 15A is connected to the inlet 17 of a mechanical filtering system 18. In the illustrate embodiment, two filtering cannisters 19 and 20 connected in series make up the filtering system 18. The outlet 18A of the filter system 18 is connected in communication with a second coil 21 which has its respective coil interposed between the coils of the first mentioned coil 15A. The outlet of the second coil 21 is indicated at 21A.

In the system 10 described, it will be apparent that the water or fluid flowing through coils 15A and 21 is subjected to the ultraviolet rays generated by the UV lamp 11 which will kill the micro-organism or bacteria present in the water or fluid being treated, and which treated water is further mechanically purified or filtered of undesirable material by further serial flow through the chemical and/or mechanical filtering cannisters 19 and 20.

In order to effectively subject the fluid or water to UV purification, it is imperative that the coils 15A and 21 be disposed in close proximity to the lamp source 11. In an intermittent water purification system, e.g. in household water use, the fluid or water being acted upon is not in constant flow. Accordingly, the water is frequently left to stand in the coils disposed about the UV lamp 11. When this occurs, the UV lamp, being in an energized state, in addition to emitting UV radiation, is also giving off heat which is also being transmitted to the water standing in the coil. Thus, as the water in the coils is being purified by the UV rays, it is also being heated by the heat generated by the lamp 11. Over prolonged standing periods, it has been noted that the standing water is subjected to and is being heated by the lamp. Such heat is undesirable when such water is being purified for drinking purposes. If the UV lamp is connected in the circuit to be cycled "off" during the non- flow period to prevent heating of the water in the non-flowing mode, the lamp would have to be cycled between "on" and "off" repeatedly which would adversely effect the life of the lamp. Also, in such situations, the water being used immediately upon flow being imparted may not be completely radiated by the UV lamp immediately upon start up.

To obviate these deficiencies in an intermittent flow situation, the lamp 11 is connected in a control circuit 25 which permits the lamp 11 to be energized to an "on" position when the starting switch 26 is actuated and which is maintained in an "on" position throughout the operating mode of the system regardless of fluid flow, and which circuit includes a means whereby the intensity of UV radiation emitted by the lamp 11 can be varied in accordance with fluid flow or demand. Thus, during periods of very low flow or at standstill, the intensity of UV generation of the lamp is materially diminished without cycling the lamp between "on" and "off" positions.

Figure 4:
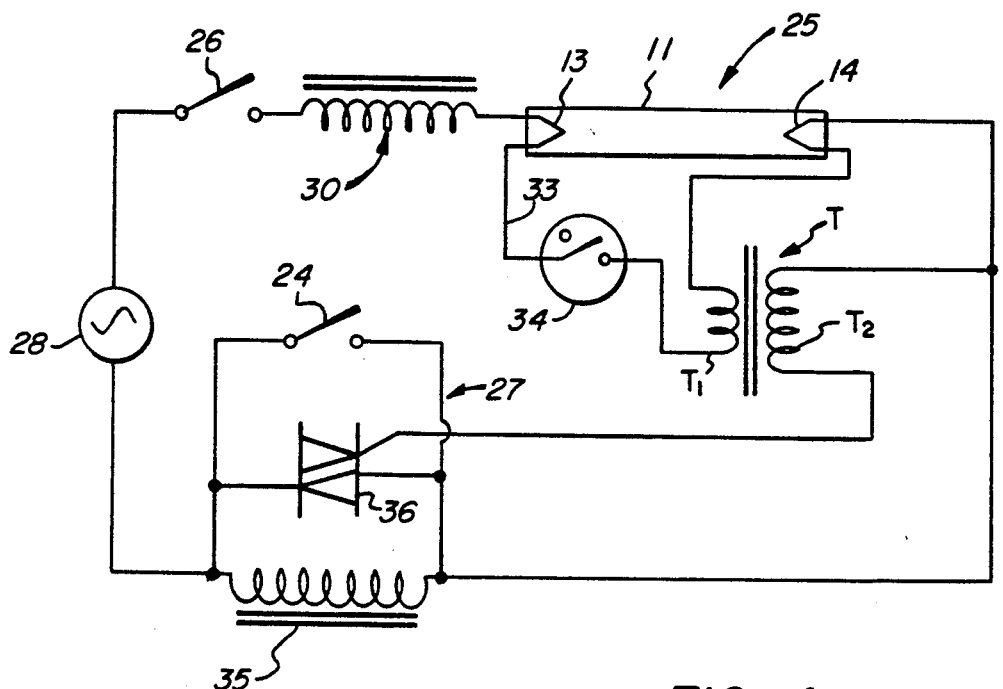
FIG. 4 is a schemmatic wiring diagram of the control circuit for varying the amount of UV generated by the lamp source in accordance with fluid flow.
Figure 3:
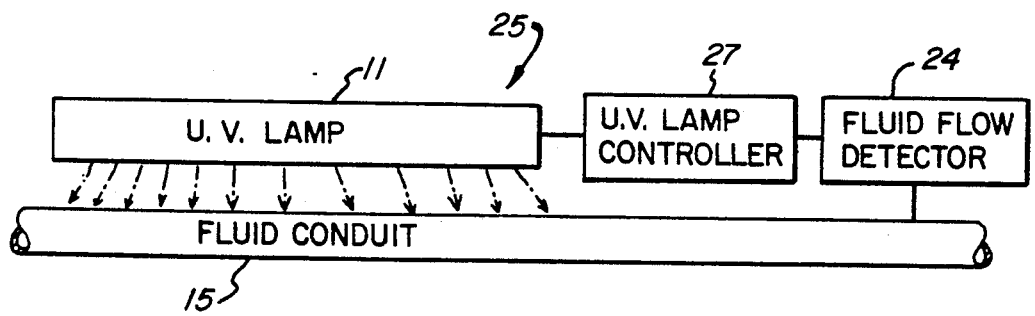
FIG. 3 is a block diagram of the control circuit utilized in the embodiment of FIGS. 1 and 2.

FIGS. 3 and 4 illustrate the control circuit 25 for energizing the lamp 11 and for regulating the amount of UV radiation emitted thereby in accordance with fluid flow.

The block diagram of FIG. 3 diagrammatically illustrates an ultraviolet lamp 11 which, when actuated, radiates UV energy to a fluid conduit or coil 15. The fluid flow within fluid conduit or coil 15 is detected by a fluid flow detector means 25. The fluid flow detector means 24 is connected in circuit to an ultraviolet lamp controller means 27 to control the intensity of the UV generation; as will be herein described.

The intensity or output of the ultraviolet lamp 11 is controlled to provide the proper amount of UV radiation to the fluid flowing within the conduit 15 or 21 so as to kill the micro-organisms therein. Additionally, the control circuit 25 is rendered more efficient because a minimum amount of energy is generated during periods of no flow or low flow; thus extending the useful life of the lamp 11, and minimizing the transfer of heat to the fluid.

The fluid flow detector 24 can be any type of detector, such as a pressure switch, float switch, hydraulic switch, mechanical switch or the like. Included in control circuit 25 is a means or circuit 27 to control the amount of UV energy generated by lamp 11 in accordance to fluid flow.

FIG. 4 illustrates a schemmatic diagram for a control circuit 25 for the UV lamp 11. The circuit illustrated in FIG. 4 is utilized to provide the operation of the lamp 11 in either a high or low operating mode. However, it will be understood that a number of intermediate settings between high or low operation can also be obtained by applying the teachings illustrated in the circuit shown in FIG. 4. An alternating current voltage source 28 is used for supplying power to the lamp circuit 25. A main switch 26 disposed in the circuit is used to energize the circuit "on" and "off." A high mode ballast 30 is connected in circuit with the switch 26 at one end. The other end of ballast 30 is connected in circuit to an electrode 13 of the UV lamp 11. In circuit with the electrodes 13 and 14 of lamp 11 is a starter circuit 33 to preheat the electrodes 13 and 14. The starter circuit 33 comprises a normally closed glow switch 34 and a transformer T, the primary $T_1$ of a transformer T being connected between the glow switch 34 and the electrode 14. The secondary $T_2$ is connected at one end in circuit with electrode 14 and at its other end to a switch means 36, e.g. an SCR or triac. As shown, the switch means or SCR or triac 36 is disposed in parallel with a low mode ballast 35. Also in parallel to the triac in a flow detection switch means 24 which when activated will cause the low mode ballast 35 to be placed in and out of the circuit and vary the intensity of the UV generation by lamp 11 accordingly.

In operation, when power is first applied to the circuit 25 by the closing of main switch 26, a voltage will be impressed onto the glow switch 34 causing the glow switch 34 to ironize. The ironization of the glow switch causes the bi-metal contact to heat up and open, the delay allowing the current to flow to the electrodes 13, 14 causing them to pre-heat. The current flowing through the closed glow switch 34 also flows through transformer primary $T_1$, causing the transformer secondary $T_2$ to be energized. This causes the high-low or triac switch 36 to close, thus shorting the low mode ballast 35 out of the circuit to the lamp. This results in the high mode ballast 30 permitting the full power required to start lamp 11 to be applied to the electrodes. Once lamp 11 is started, glow switch 34 opens, eliminating the current flow to transformer primary $T_1$, thereby removing the induced current to the transformer secondary $T_2$. When this occurs, the triac 36 is opened, causing current to flow to the low mode ballast 35, placing the low mode ballast 35 in circuit with the high mode ballast at which time the circuit is operating in a low mode, wherein the lamp 11 is in an energized state, but emitting very little ultraviolet energy. When a fluid demand is made on the system, the flow detective switch 24, in sensing flow, closes and takes the ballast 35 out of the circuit. With the low mode ballast out of the circuit, the amount of UV emitted by the lamp 11 is increased to place the circuit in high mode operation. When the high-low switch 36 is closed, the low mode ballast 35 is by-passed or shorted, resulting in the high current ballast 30 controlling the energy of lamp 11. As can be seen, the circuit illustrated in FIG. 4 has the advantage in that the lamp 11 is always started by the high mode ballast 30 regardless of what positioned the high-low switch 36 is in; and the low mode ballast 35 is placed into and out of the circuit depending upon the position of the flow detection switch 24, to vary the intensity of the UV generation by lamp 11.

The principles taught in the circuit illustrated in FIG. 4 can easily be applied for providing a circuit having a multiple of power levels that can be applied to lamp 11. A plurality of ballasts can be used in conjunction with a plurality of high-low or shorting switches so as to provide multiple intermediate power levels for the lamp between high mode and low mode. However, regardless of the number of power levels, the initial starting of the lamp is always activated by the high mode ballast 30.

From the foregoing, it will be apparent that the UV lamp 11 is activated in a pre-heat mode, and that the intensity or amount of UV energy generated thereby can be varied by the actuation of the flow switch 24 which is disposed in a circuit containing a second or low mode ballast 35 which is placed out of the lamp circuit whenever the flow switch 24 is opened or closed according to fluid flow. Actuation of the flow switch 24, after the lamp has been energized or started, places the ballast 35 in and out of the circuit with the starting ballast 30 and the intensity of lamp 11 is varied as to the amount of UV energy generated. Thus, the amount of UV generation is varied in accordance with flow without cycling the lamp between its "on" or "off" positions. In the circuit described, the high-low switch or triac 36 is maintained in its closed position during the pre-heat cycle of the lamp. Once the lamp 11 is started, the triac 36 is opened to ready the second ballast 35.

Figure 2:
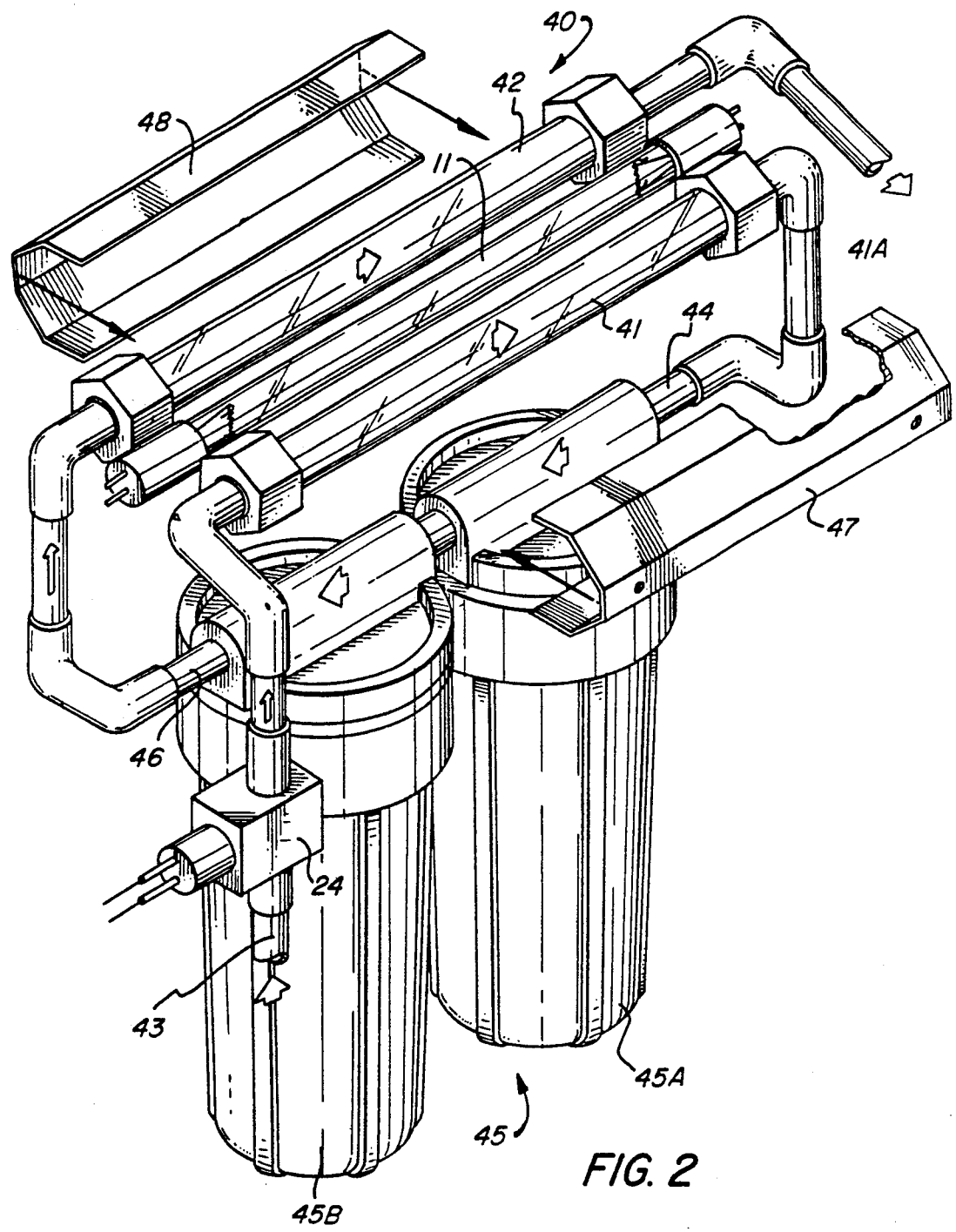
FIG. 2 is a perspective view of another water purification system embodying the invention.

FIG. 2 illustrates a further embodiment of the invention. In this form of the invention, the purification system 40 is similar in all respects to that described and shown in FIG. 1 with the exception that instead of flowing the fluid to be acted upon through UV pervious coils 15 and 21 as described in FIG. 1, the fluid to be treated is directed through elongated conduits 41 and 42. As for example, the fluid inlet 43 from the reservoir (not shown) is connected in communication with a conduit 41 disposed in UV transmitting relationship to the UV lamp 11. The outlet end 41A of conduit 41 connected to the inlet 42 of the mechanical filtering means 45, i.e. cannister 45A. Serially connected to cannister 45A is a second filtering cannister 45B, the outlet 46 of which is connected to the second conduit 42. The arrangement is such that the UV energy generated by lamp 11 is transmitted to the fluid flowing through the UV pervious conduits 41 and 42. To maximize the absorption of the UV radiation by the fluid flowing through conduits 41 and 42, reflecting shields 47 and 48 are disposed about conduits 41 and 42 respectively. As shown, the reflector shields 47 and 48 are generally U-shaped that are open toward the lamp 11.

The control circuit as described with respect to FIGS. 3 and 4 controls the actuation of the lamp as hereinbefore described. In all other respects, the construction and operation of the embodiment of FIG. 2 is similar to that described with respect to FIG. 1.

While the invention has been described in conjunction with a potable purification system, the same principle can be applied to industrial waste water treating facilities wherein relatively large banks of UV lamps are employed. Heretofore, the amount of UV radiation generated in such system was controlled by the amount or number of lamps or banks of lamps that are energized under any given condition. Thus, the lamps disposed in such banks were either on or off depending upon fluid flow. By utilizing the teaching of this invention, the lamps in the respective bank can be disposed in a circuit utilizing a control circuit as described with respect to FIG. 3 so as to include a low mode ballast wired as herein described to vary the intensity of the UV lamps to vary the amount of UV generation. In this manner, the number of banks required in such prior known industrial waste water treating facilities can be reduced since the present invention allows for a single bank of lamps whereby the intensity of the respective lamps can be varied according to flow.

While the invention has been described with respect to several embodiments, it will be understood and appreciated by those who are skilled in the art that variation and modifications may be made without departing from the spirit and scope of the invention.

What is claimed is:
1. An ultraviolet purification system comprising
a source of UV radiation,
conduit means through which fluid to be acted upon flows is disposed in UV transmitting relationship to said radiation source,
a first ballast connected in circuit with said source of UV radiation,
a starting circuit means connected between said ballast and said source, a second ballast, and a control circuit responsive to the flow of fluid through said conduit means connected to said second ballast to vary the amount of UV radiation generated by said source in accordance with the amount of fluid flowing through said conduit means whereby said source is maintained in an energized state regardless of the amount of fluid flow.

2. An ultraviolet purification system comprising a source of UV radiation, conduit means through which fluid to be acted upon flows is disposed in UV transmitting relationship to said radiation source, and a control means for controlling that amount of UV radiation emitted by said radiation source in accordance with fluid flow through said conduit means, said control means includes a circuit having a ballast connected in circuit with said source of UV radiation, a starter circuit means connected between said ballast and said source, said starter circuit includes a starting switch means connected in circuit to said source of UV radiation, a transformer having a primary and secondary, said primary being connected to said radiation source and said starting switch means, and said secondary being connected in a circuit to said radiation source and a control circuit connected in circuit to said secondary responsive to the flow of fluid through said conduit means connected to said ballast to vary the amount of UV radiation generated by said source in accordance with the amount of fluid flowing through said conduit means whereby said source is maintained in an energized state regardless of the amount of fluid flow.

3. An ultraviolet purification system comprising:

a source of UV radiation, conduit means through which fluid to be acted upon flows is disposed in UV transmitting relationship to said radiation source, a control means for controlling that amount of UV radiation emitted by said radiation source in accordance with fluid flow through said conduit means, said control means includes a circuit having a ballast connected in circuit with said source of UV radiation, a starter circuit means connected between said ballast and said source, and a control circuit responsive to the flow of fluid through said conduit means connected to said ballast to vary the amount of UV radiation generated by said source in accordance with the amount of fluid flowing through said conduit means, said control circuit includes a second ballast connected in circuit with said radiation source and in series with said first mentioned ballast, a flow detection switch means responsive to fluid flow connected in parallel with said second ballast, and a ballast switching means connected in parallel with said flow detection switch means and said second ballast whereby said ballast switching means is activated upon the actuation of said radiation source to ready said second ballast in response to the actuation of said flow detection switch, whereby said source is maintained in an energized state regardless of the amount of fluid flow.

4. An ultraviolet purification system as defined in claim 3 wherein said conduit means includes a coil circumscribing said radiation source, said conduit means having an outlet end, and filtering cannister connected in communication with said outlet end of said conduit means.

5. An ultraviolet purification system as defined in claim 3 wherein said conduit means comprises an elongated tubular conduit disposed in longitudinal UV transmitting relationship to said radiation source; and said conduit means having a fluid outlet, and a filtering cannister connected in communication with said outlet.

6. An ultraviolet purification system comprising:

an ultraviolet lamp having a pair of opposed electrodes, conduit means impervious to ultraviolet radiation for conducting fluid to be acted upon disposed in ultraviolet transmitting relationship to said lamp and a control circuit means for controlling the amount of ultraviolet radiation transmitted to the fluid in accordance to the flow rate thereof, said control circuit means including a first ballast connected in circuit with one of said electrodes, a starting circuit connected to the electrodes of said lamp, said starting circuit including a starting switch means connected in circuit with said one electrode; and a transformer, said transformer having a primary connected in circuit with the other of said electrodes and said starting switch means, a flow responsive control circuit, said transformer having a secondary connected in circuit with said other electrode and said control circuit, a secondary ballast connected in circuit with said other electrode and said first ballast, a ballast switch means connected across said second ballast, and a flow detection switch connected in parallel with said ballast switch, and said second ballast whereby said ballast switch means is activated upon the actuation of said ultraviolet lamp to ready said second ballast in response to the actuation of said flow detection switch to vary the radiation output of said lamp.

7. An ultraviolet purification system comprising:

a source of UV radiation;

a conduit means, positioned adjacent said source of UV radiation, for conducting fluid to be purified;

a high mode ballast connected to said source;

a starter circuit connected to said source and said high mode ballast;

a transformer having a primary and a secondary, said primary connected to said starter circuit;

a low mode ballast connected to said source and the secondary of said transformer;

a first switch in parallel with said low mode ballast and connected to the secondary;

a second switch in parallel with said ballast; and a fluid flow detector connected to and controlling the second switch, whereby said source is always started with said high mode ballast irrespective of the condition of said second switch.

8. An ultraviolet purification system as in claim 7 wherein said first switch comprises:

a triac.

* * * * *